(12) United States Patent
Sliwa et al.

(10) Patent No.: US 11,439,460 B2
(45) Date of Patent: Sep. 13, 2022

(54) CATHETER SYSTEM AND ELECTRODE ASSEMBLY FOR INTRAPROCEDURAL EVALUATION OF RENAL DENERVATION

(71) Applicant: St. Jude Medical, Cardiology Division, Inc., St. Paul, MN (US)

(72) Inventors: John Sliwa, San Jose, CA (US); Stephen A. Morse, Menlo Park, CA (US); Cary Hata, Irvine, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1127 days.

(21) Appl. No.: 15/630,134

(22) Filed: Jun. 22, 2017

(65) Prior Publication Data
US 2017/0367756 A1 Dec. 28, 2017

Related U.S. Application Data

(60) Provisional application No. 62/353,606, filed on Jun. 23, 2016.

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/0215* (2013.01); *A61B 5/4836* (2013.01);
(Continued)

(58) Field of Classification Search
CPC .......... A61B 2018/00214; A61B 2018/00267; A61B 5/6858; A61B 5/6859;
(Continued)

(56) References Cited

U.S. PATENT DOCUMENTS

| 3,650,277 A | 3/1972 | Sjostrand et al. |
| 4,658,819 A | 4/1987 | Harris et al. |

(Continued)

FOREIGN PATENT DOCUMENTS

| WO | 97/45157 | 12/1997 |
| WO | 00/66020 | 11/2000 |

(Continued)

OTHER PUBLICATIONS

International Search Report and Written Opinion for International Patent Application No. PCT/US2017/038659, dated Oct. 4, 2017, 14 pages.

(Continued)

*Primary Examiner* — Michael F Peffley
*Assistant Examiner* — Samantha M Good
(74) *Attorney, Agent, or Firm* — Armstrong Teasdale LLP

(57) ABSTRACT

The present disclosure provides catheter systems, electrode assemblies, and methods for electrically stimulating one or more points about the circumference of the renal artery to provide real time intraprocedural operational feedback to the operator of a renal denervation procedure to allow for more precise and thorough ablation of the renal artery and better patient outcomes. In many embodiments, an electrode assembly is provided that includes multiple splines that extend from an insulated proximal hub to an insulated distal hub and are interconnected to an electrical wire to allow the splines to independently function as electrical stimulation electrodes. The electrically active splines can then be energized at one or more desired points during a renal denervation procedure to provide operational feedback.

10 Claims, 8 Drawing Sheets

(51) Int. Cl.
*A61B 5/0215* (2006.01)
*A61N 7/02* (2006.01)
*A61B 17/00* (2006.01)
*A61B 5/20* (2006.01)
*A61B 18/00* (2006.01)
*A61N 7/00* (2006.01)

(52) U.S. Cl.
CPC .......... *A61B 5/6858* (2013.01); *A61B 5/6859* (2013.01); *A61N 7/02* (2013.01); *A61B 5/201* (2013.01); *A61B 2017/00039* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00642* (2013.01); *A61B 2018/00821* (2013.01); *A61B 2018/00839* (2013.01); *A61B 2018/00863* (2013.01); *A61B 2018/00988* (2013.01); *A61B 2018/1465* (2013.01); *A61B 2018/1467* (2013.01); *A61N 2007/003* (2013.01)

(58) Field of Classification Search
CPC ... A61B 18/1492; A61B 5/0215; A61B 5/201; A61B 5/4836; A61B 2018/00404; A61B 2018/00434; A61B 2018/00511; A61B 2018/00577; A61N 7/02
See application file for complete search history.

(56) References Cited

U.S. PATENT DOCUMENTS

| | | |
|---|---|---|
| 5,035,694 A | 7/1991 | Kasprzyk et al. |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,283,988 B1 * | 9/2001 | Laufer ................... A61B 18/00 607/101 |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hedge et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 2002/0068885 A1 | 6/2002 | Harhen et al. |
| 2002/0120304 A1 | 8/2002 | Mest |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0288730 A1 | 12/2005 | Deem |
| 2006/0089678 A1 | 4/2006 | Shalev |
| 2007/0135875 A1 | 6/2007 | Demarais et al. |
| 2008/0255478 A1 | 10/2008 | Burdette |
| 2009/0076409 A1 | 3/2009 | Wu et al. |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2011/0306851 A1 * | 12/2011 | Wang ................ A61B 18/1492 600/301 |
| 2012/0071870 A1 * | 3/2012 | Salahieh ............ A61B 1/00181 606/33 |
| 2012/0143097 A1 | 6/2012 | Pike, Jr. |
| 2012/0143298 A1 | 6/2012 | Just et al. |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |
| 2014/0025069 A1 | 1/2014 | Willard et al. |
| 2014/0200578 A1 | 7/2014 | Groff et al. |
| 2014/0303617 A1 | 10/2014 | Shimada |
| 2014/0350553 A1 * | 11/2014 | Okuyama ........... A61B 18/1492 606/41 |

(56) References Cited

U.S. PATENT DOCUMENTS

2015/0045863 A1* 2/2015 Litscher ............ A61B 18/1492
607/116

FOREIGN PATENT DOCUMENTS

| WO | 01/00273 | 1/2001 |
| --- | --- | --- |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012068471 A1 | 5/2012 |
| WO | 2012/106492 | 8/2012 |

OTHER PUBLICATIONS

Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.

Hall, Winthrop H. et al, Combined Embolization and Percutaneous Radiofrequency Ablation of a Solid Renal Tumor, American Journal of Roentgenology, 174, Jun. 2000, 1592-1594.

Hall, J.E. et al, Role of Sympathetic Nervous System and Neuropeptides in Obesity Hypertension, Brazilian Journal of Medical and Biological Research, 2000, 33:605-618.

Han, Young-Min et al, Renal Artery Embolization with Diluted Hot Contrast Medium: An Experimental Study, Journal of Vascular and Interventional Radiology, Jul. 2001;12(7):862-868.

Hansen, Jesper Melchoir et al, The Transplanted Human Kidney Does Not Achieve Functional Reinnervation, Clinical Science, (1994) 87, 13-20.

Heuer, George J., The Surgical Treatment of Essential Hypertension, Annals of Surgery, Oct. 1936, vol. 104, No. 3, 771-786.

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of The American Heart Association, vol. IV, Aug. 1951, 173-183.

Hoye, Neil A. et al., Endovascular Renal Denervation: A Novel Sympatholytic with Relevance to Chronic Kidney Disease, Clinical Kidney Journal Advance Access, (2013) 0: 1-8.

Huang, Wann-Chu, Renal Denervation Prevents and Reverses Hyperinsulinemia-lnduced Hypertension in Rats, Hypertension Journal of The American Heart Association, 1998;32:249-254.

Huang, Shoei K. Stephen et al, Radiofrequency Catheter Ablation of Cardiac Arrhythmias, Basic Concepts and Clinical Applications, Wiley-Blackwell, Jun. 2000, 1-12.

Humpreys, Michael H., Renal Nerves and CKD: Is Renal Denervation the Answer?, Journal of The American Socity of Nephrology, 2012, 23: 1-3.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyte Metab 1989;15:74-82.

Kaltenbach, Benjamin et al, Renal Sympathetic Denervation as Second-Line Therapy in Mild Resistant Hypertension: A Pilot Study, Catheterization and Cardiovascular Interventions 81:335-339 (2013).

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the Symplicity HTN-3 Trial, Clin. Cardiol. 35, 9, 528-535 (2012).

Kapural, Leonardo et al, Radiofrequency Ablation for Chronic Pain Control, Current Pain and Headache Reports 2001, 5:517-525.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katritsis, Demosthenes et al, Recurrence of Left Atrium-Pulmonary Vein Conduction Following Successful Disconnection in Asymptomatic Patients, Europace (2004) 6, 425e432.

Killip III, Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, GE et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.

Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

(56) References Cited

OTHER PUBLICATIONS

Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mancia, Giuseppe et al, Sympathetic Activation in the Pathogenesis of Hypertension and Progression of Organ Damage, Hypertension Journal of The American Heart Association, 1999, 34:724-728.
Medtronic, Inc., Renal Denervation (RDN) Novel Catheter-based Treatment for Hypertension, Symplicity RDN System Common Q&A, 2011.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Millard, F.C. et al, Renal Embolization for Ablation of Function in Renal Failure and Hypertension, Postgraduate Medical Journal (1989) 65, 729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al, 1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thomas, George et al, Renal Denervation to Treat Resistant Hypertension: Guarded Optimism, Cleveland Clinic Journal of Medicine, vol. 79, No. 7, Jul. 2012, 501-510.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
De Wardener, H.E., The Hypothalamus and Hypertension, Physiological Reviews,vol. 81, No. 4, Oct. 2001.
Webb, R.L. et al, Functional Identification of the Central Projections of Afferent Renal Nerves, Clin. and Exper.-Theory and Practice, Ag(SUPPL.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Zazgornik, Jan et al, Bilateral Nephrectomy: The Best, but Often Overlooked, Treatment for Refractory Hypertension in Hemodialysis Patients, AJH 1998; 11:1364-1370.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Worthley, Stephen G. et al, Renal Denervation: How Do You Measure Success?, presentation 28 pages.
International Search Report and Written Opinion for Application No. PCT/US2010/054637.
International Search Report and Written Opinion for Application No. PCT/US2010/054684.
Dibona, Gerald F., Role of the Renal Nerves in Renal Sodium Retention and Edema Formation, Trans Am Clin Climatol Assoc. 1990; 101: 38-45.
Perry, C. Bruce, Malignant Hypertension Cured by Unilateral Nephrectomy, British Heart Journal, Jul. 1945; 7(3): 139-142.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Page, Irvine H. et al, Mechanisms, Diagnosis and Treatment of Hypertension of Renal Vascular Origin; Annals of Internal Medicine, Aug. 1959;51:196-211.
Canadian Agency for Drugs and Technologies in Health, Catheter-Based Renal Denervation for Treatment-Resistant Hypertension; Issues in Emerging Health Technologies, Issue 121, Mar. 2013.

(56) References Cited

OTHER PUBLICATIONS

Meredith, I T et al, Exercise Training Lowers Resting Renal But Not Cardiac Sympathetic Activity in Humans; Hypertension Journal of The American Heart Association, 1991;18:575-582.
Garel, L. et al, Fatal Outcome After Ethanol Renal Ablation in Child with End-Stage Kidneys; AJR 146:593-594, Mar. 1986.
Oparil, Suzanne et al, Renal Nerve Ablation: Emerging Role in Therapeutics; Blood Pressure, Oct. 2011, vol. 20, No. 5, pp. 253-255.
Dibona, Gerald F., Sympathetic Nervous System and Hypertension, Hypertension Journal of The American Heart Association, 2013; 61: 556-560.
Persu, Alexandre et al, Renal Denervation: Ultima Ratio or Standard in Treatment-Resistant Hypertension, Hypertension Journal of The American Heart Association, Sep. 2012;60(3):596-606.
Doumas, Michael et al, Interventional Management of Resistant Hypertension, The Lancet, vol. 373, Apr. 11, 2009, pp. 1228-1230.
Schmieder, Roland E. et al, Updated EHS Position Paper on Interventional Therapy of Resistant Hypertension, EuroIntervention 2013; 9:R58-R66.
Calleary, Hickey D. et al, Pre-Transplant Bilateral Native Nephrectomy for Medically Refractory Hypertension, The Irish Medical Journal, Jul.-Aug. 2001;94(7):214-6.
Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
Blankestijn, Peter J. et al, Renal Denervation: Potential Impact on Hypertension in Kidney Disease?, Nephrol Dial Transplant (2011) 0: 1-3.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Smith, Harold P. et al, Radiofrequency Neurolysis in a Clinical Model Neuropathological Correlation, J Neurosurg 55:246-253, 1981.
Young, Robert R. et al, Reversible Block of Nerve Conduction by Ultrasound Ultrasonic Blocking of Nerve Fibers, Arch Neurol. 1961;4(1):83-89.
Wolf-Maier, Katharina et al, Hypertension Treatment and Control in Five European Countries, Canada, and the United States, Hypertension. 2004;43:10-17.
Elmula, Fadl et al, Renal Sympathetic Denervation in Patients With Treatment-Resistant Hypertension After Witnessed Intake of Medication Before Qualifying Ambulatory Blood Pressure, Hypertension 2013;62:526-532.
Santos, Mario et al, Renal Sympathetic Denervation in Resistant Hypertension, World J Cardiol Apr. 26, 2013; 5(4):94-101.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bao, Gang et al, Blood Pressure Response to Chronic Episodic Hypoxia: Role of the Sympathetic Nervous System, American Journal of Physiology, 1997, 95-101.

Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, Vito M. et al, Renal Afferent Denervation Prevents Hypertension in Rats With Chronic Renal Failure, Hypertension, 1995, 25, 878-882.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dequattro V. et al, The Sympathetic Nervous System: The Muse of Primary Hypertension, Journal of Human Hypertension, 2002, 16 (Suppl 1), S64-S69.

(56) References Cited

OTHER PUBLICATIONS

Dibona, Gerald F., Neural Control of the Kidney: Functionally Specific Renal Sympathetic Nerve Fibers, American Journal of Physiology, 2000, 279, R1517-R1524.

Dibona, Gerald F. et al, Translational Medicine: The Antihypertensive Effect of Renal Denervation, Americal Journal of Physiology, 2010, 298, R245-R253.

Dibona, Gerald F. et al, Neural Control of Renal Function, Physiological Reviews, vol. 77, No. 1, Jan. 1997, 75-197.

Dibona, Gerald F., Renal Innervation and Denervation: Lessons from Renal Transplantation Reconsidered, Artificial Organs, vol. 11, No. 6, 1987, 457-462.

Dibona, Gerald F., Neural Control of Renal Function: Cardiovascular Implications, Hypertension Journal of the American Heart Association, vol. 13, No. 6, Part 1, Jun. 1989, 539-548.

Dibona, Gerald F., Neural Control of the Kidney: Past, Present, and Future, Hypertension Journal of the American Heart Association, vol. 41, Mar. 2003, Part II, 621-624.

Dibona, Gerald F., The Sympathetic Nervous System and Hypertension, Hypertension Journal of The American Heart Association, vol. 43, Feb. 2004, 147-150.

Dubuc, Marc et al, Feasibility of Cardiac Cryoablation Using a Transvenous Steerable Electrode Catheter, Journal of Interventional Cardiac Electrophysiology, 1998, 2: 285-292.

Esler, M. et al, Sympathetic Nerve Activity and Neurotransmitter Release in Humans: Translation from Pathophysiology into Clinical Practice, Scandinavian Physiological Society, 2003, 177, 275-284.

Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.

Evelyn, Kenneth A. et al, Effect of Thoracolumbar Sympathectomy on the Clinical Course of Primary (Essential) Hypertension, American Journal of Medicine, Feb. 1960, 188-221.

Freyberg, R. H. et al, The Effect on the Kidney of Bilateral Splanchnicectomy in Patients with Hypertension, The Journal of Clinical Investigation, vol. 16, Issue 1, Jan. 1937, 49-65.

Gazdar, A. F. et al, Neural Degeneration and Regeneration in Human Renal Transplants, The New England Journal of Medicine, vol. 238, No. 5, Jul. 1970, 222-224.

Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.

Gorisch, Wolfram et al, Heat-Induced Contraction of Blood Vessels, Lasers in Surgery and Medicine 2:I-13 (1982).

Grassi, Guido et al, Baroreflex Control of Sympathetic Nerve Activity in Essential and Secondary Hypertension, Hypertension Journal of The American Heart Association, 1998;31:68-72.

Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.

Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.

Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.

Guyton, Arthur C., Blood Pressure Control Special Role of the Kidneys and Body Fluids, Science, vol. 252, Jun. 1991, 1813-1816.

Medtronic, Inc., J.P. Morgan Healthcare Conference, Corrected Transcript, Jan. 13, 2014, Factset:Callstreet, www.callstreet.com.

Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.

Morrissey, D.M. et al, Sympathectomy in the Treatment of Hypertension, The Lancet, Feb. 1953, 403-408.

Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.

Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).

Naidoo, N. et al, Thoracic Splanchnic Nerves: Implications for Splanchnic Denervation, Journal of Anatomy, Nov. 2001;199(Pt 5):585-590.

Nakagawa, Hiroshi et al, Inverse Relationship Between Electrode Size and Lesion Size During Radiofrequency Ablation With Active Electrode Cooling, Circulation. Aug. 4, 1998;98(5):458-465.

Nakagawa, A. et al, Selective Ablation of Porcine and Rabbit Liver Tissue Using Radiofrequency: Preclinical Study, European Surgical Research, 1999;31:371-379.

Nanni, Gregg S. et al, Control of Hypertension by Ethanol Renal Ablation, Radiology 148: 51-54, Jul. 1983.

Ndegwa, S., Catheter-Based Renal Denervation for Treatment-Resistant Hypertension [Issues in emerging health technologies issue 121]. Ottawa: Canadian Agency for Drugs and Technologies in Health; 2013.

Neutel, Joel M., Hypertension and Its Management: A Problem in Need of New Treatment Strategies, Journal of Renin-Angiotensin-Aldosterone System 2000 1: S10-S13.

Newcombe, C.P. et al, Sympathectomy for Hypertension, British Medical Journal, Jan. 1959, 142-144.

Ng, Fu Siong et al, Catheter Ablation of Atrial Fibrillation, Clinical Cardiology, 25, 384-394 (2002).

Norman, Roger A. et al, Role of the Renal Nerves in One-Kidney, One Clip Hypertension in Rats, Hypertension Journal of The American Heart Association, 1984;6:622-626.

Nozawa, Takashi et al, Effects of Long-Term Renal Sympathetic Denervation on Heart Failure After Myocardial Infarction in Rats, Heart Vessels (2002) 16:51-56.

O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.

O'Hagen, Kathleen P. et al, Renal Denervation Decreases Blood Pressure in DOCA-Treated Miniature Swine With Established Hypertension, American Journal of Hypertension, 1990; 3:62-64.

Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.

Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.

Oral, Hakan et al, Pulmonary Vein Isolation for Paroxysmal and Persistent Atrial Fibrillation, Circulation Journal of The American Heart Association, 2002;105:1077-1081.

Osborn, Jeffrey L. et al, Long-Term Increases in Renal Sympathetic Nerve Activity and Hypertension, Clinical and Experimental Pharmacology and Physiology (1997) 24,72-76.

Osborn, John W., The Sympathetic Nervous System and Long-Term Regulation of Arterial Pressure: What Are the Critical Questions?, Clinical and Experimental Pharmacology and Physiology (1997) 24, 68-71.

Ou, Baiqing et al, Baroreflex Sensitivity Predicts the Induction of Ventricular Arrhythmias by Cesium Chloride in Rabbits, Japanese Circulation Journal, 1999; 63: 783-788.

Page, Irvine H. et al, Mechanisms, Diagnosis and Treatment of Hypertension of Renal Vascular Origin, Annal of Internal Medicine, Aug. 1959, vol. 51, No. 2, 196-211.

Page, Max, Section of Surgery, Discussion on the Surgical Treatment of Hypertension, Proceedings of the Royal Society of Medicine, vol. XLI, Feb. 1948, 359-372.

(56) References Cited

OTHER PUBLICATIONS

Page, Irvine H. et al, The Effect of Renal Denervation on the Level of Arterial Blood Pressure and Renal Function in Essential Hypertension, Journal of Clinical Investigation, 1935;14(1):27-30.

Page, Irvine H., The Effect of Renal Efficiency of Lowering Arterial Blood Pressure in Cases of Essential Hypertension and Nephritis, Journal of Clinical Investigation, Nov. 1934; 13(6): 909-915.

Papademetriou, Vasilios, Hypertension and the Simplicity Renal Denervation System, Scientific Background, www.medtronic.com, 2011.

Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.

Parati, Gianfranco et al, The Human Sympathetic Nervous System: Its Relevance in Hypertension and Heart Failure, European Heart Journal (2012) 33, 1058-1066.

Pearce, John A. et al, Blood Vessel Architectural Features and Their Effect on Thermal Phenomena, Critical Reviews, vol. CR75, 231-277.

Peet, Max Minor, Hypertension and Its Surgical Treatment by Bilateral Supradiaphragmatic Splanchnicectomy, American Journal of Surgery, vol. 75, Issue 1, Jan. 1948, 48-68.

Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.

Plouin, Pierre-Francois et al, Blood Pressure Outcome of Angioplasty in Atherosclerotic Renal Artery Stenosis A Randomized Trial, Hypertension Journal of The American Heart Association, 1998;31:823-829.

Poutasse, Eugene F., Surgical Treatment of Renal Hypertension, American Journal of Surgery, vol. 107, Jan. 1964, 97-103.

Pugsley, M.K. et al, The Vascular System An Overview of Structure and Function, Journal of Pharmacological and Toxicological Methods 44 (2000) 333-340.

Rippy, Marian K. et al, Catheter-Based Renal Sympathetic Denervation: Chronic Preclinical Evidence for Renal Artery Safety, Clin Res Cardiol (2011) 100:1095-1101.

Ritz, Eberhard, New Approaches to Pathogenesis and Management of Hypertension, Clin J Am Soc Nephrol 4: 1886-1891, 2009.

Robbins, Ivan M. et al, Pulmonary Vein Stenosis After Catheter Ablation of Atrial Fibrillation, Circulation Journal of The American Heart Association, 1998;98:1769-1775.

Rocha-Singh, Krishna J., Catheter-Based Sympathetic Renal Denervation A Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

Schauerte, Patrick et al, Catheter Ablation of Cardiac Autonomic Nerves for Prevention of Vagal Atrial Fibrillation, Circulation Journal of The American Heart Association, 2000, 102:2774-2780.

Schlaich, Markus P. et al, Renal Denervation as a Therapeutic Approach for Hypertension Novel Implications for an Old Concept, Hypertension Journal of The American Heart Association, 2009;54:1195-1201.

Schlaich, Markus P. et al, Renal Sympathetic-Nerve Ablation for Uncontrolled Hypertension, The New England Journal of Medicine, 2009; 361:932-934.

Schmieder, Roland E. et al, ESH Position Paper: Renal Denervation—An Iterventional Therapy of Resistant Hypertension, Journal of Hypertension, 2012, 30:837-841.

Sellers, Alfred M. et al, Adrenalectomy and Sympathectomy for Hypertension Ten Year Survival, Archives of Surgery, vol. 89, Nov. 1964, 880-886.

Sen, S.K., Some Observations on Decapsulation and Denervation of the Kidney, The British Journal of Urology, vol. 8, Issue 4, Dec. 1936, 319-328.

Shiraki, Iwao William, Correction of Renal Hypertension by Ligation of Stenotic Segmental Renal Artery, Urology, vol. IX, No. 3, Mar. 1977, 296-298.

Shonai, Takaharu et al, Renal Artery Aneurysm: Evaluation with Color Doppler Ultrasonography Before and After Percutaneous Transarterial Embolization, J Ultrasound Med 19:277-280, 2000.

Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.

Brinkmann, Julia et al, Catheter-Based Renal Nerve Ablation and Centrally Generated Sympathetic Activity in Difficult-to-Control Hypertensive Patients Prospective Case Series, Hypertension 2012;60:1485-1490.

Jin, Yu et al, No Support for Renal Denervation in a Meta-Analysis, JACC vol. 62, No. 21, 2013 Correspondence Nov. 19/26, 2013:2029-30.

Howard, James P. et al, Size of Blood Pressure Reduction from Renal Denervation: Insights from Meta-Analysis of Antihypertensive Drug Trials of 4121 Patients with Focus on Trial Design: the CONVERGE Report, Heart 2013;0:1-9.

Mahfoud, Felix et al, Expert Consensus Document from the European Society of Cardiology on Catheter-Based Renal Denervation, European Heart Journal, Jul. 2013;34(28):2149-57.

Howell, Marcus H. et al, Tandem Stenting of Crossed Renal Arteries with Ostial Stenosis, Tex Heart Inst J. 2000; 27(2): 166-169.

Gafoor, Sameer et al, Nonresponders to Renal Denervation for Resistant Hypertension, Endovascular Today, Oct. 2013, 63-70.

Vonend, Oliver et al, Secondary Rise in Blood Pressure After Renal Denervation, The Lancet, vol. 380, Issue 9843, p. 778, Aug. 25, 2012.

Kaltenbach, Benjamin et al, Renal Artery Stenosis After Renal Sympathetic Denervation, J Am Coll Cardiol. Dec. 25, 2012;60(25):2694-5.

McGahan, John P. et al, History of Ablation, Tumor Ablation, 2005, pp. 3-16.

Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.

Crile, George, The Clinical Results of Celiac Ganglionectomy in the Treatment of Essential Hypertension, Annals of Surgery, Jun. 1938; 107(6): 909-916.

Lambert, Gavin W. et al, Health-Related Quality of Life After Renal Denervation in Patients With Treatment-Resistant Hypertension, Hypertension. 2012;60:1479-1484.

Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.

Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.

Krum, Henry et al, Device-Based Antihypertensive Therapy: Therapeutic Modulation of the Autonomic Nervous System, Circulation. 2011;123:209-215.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.

(56) References Cited

OTHER PUBLICATIONS

Campese, Vito M., Interventional Hypertension: A New Hope or a New Hype? The Need to Redefine Resistant Hypertension, J Hypertens. Nov. 2013;31(11):2118-21.
Katholi, Richard E. et al, Role of the Renal Nerves in the Pathogenesis of One-Kidney Renal Hypertension in the Rat, Hypertension. 1981;3:404-409.
Dailey, U.G., The Surgical Treatment Of Hypertension: A Review, Journal of the National Medical Association, Mar. 1948, vol. 40, No. 2, 76-79.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Page, Irvine H. et al, The Effects of Renal Denervation on Patients Suffering from Nephritis, J Clin Invest. 1935;14(4):443-458.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Putney, John Paul, Are Secondary Considerations Still "Secondary"?:An Examination of Objective Indicia of Nonobviousness Five Years After KSR, Intellectual Property Brief, vol. 4, Issue 2, Article 5, 2012, 45-59.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Hall, John E., The Kidney, Hypertension, and Obesity, Hypertension. 2003;41:625-633.
Pavlovich, Christian P. et al, Percutaneous Radio Requency Ablation of Small Renal Tumors: Initial Results; The Journal of Urology, vol. 167, 10-15, Jan. 2002.
Kassab, Salah et al, Renal Denervation Attenuates the Sodium Retention and Hypertension Associated with Obesity, Hypertension vol. 25, No. 4, Part 2 Apr. 1995.
Grassi, Guido et al, Dissociation Between Muscle and Skin Sympathetic Nerve Activity in Essential Hypertension, Obesity, and Congestive Heart Failure, Hypertension. 1998;31:64-67.
Goldberg, Michael R. et al, Reconstructive Vascular Surgery for Renovascular Hypertension, Can Med Assoc J. Feb. 2, 1974;110(3):275-80.
Michaelis, Lawrence L. et al, Effects of Renal Denervation and Renin Depletion on the Renal Responses to Intravascular Volume Expansion, Ann Surg. Mar. 1972; 175(3): 424-430.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Luscher, Thomas F. et al, Renal Nerve Ablation After SYMPLICITY HTN-3: Confused at the Higher Level?; European Heart Journal, doi:10.1093/eurheartj/ehu195; May 14, 2014.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Thiebot, J. et al, Bilateral Nephrectomy by Embolization of the Renal Arteries: A Report on Five Cases (author's transl), Sem Hop. Apr. 8-15, 1980;56(13-14):670-5.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Moss, Jonathan, Interventional Radiology and Renal Denervation, Interventions, vol. 13, Issue 3, 2013.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Dibona, Gerald F., Sympathetic Nervous System and the Kidney in Hypertension, Curr Opin Nephrol Hypertens. Mar. 2002;11(2):197-200.
Hamm, Christian et al, Confluence, Issue eight, Apr. 2014.
Parmar, Arundhati, Analyst: Medtronic Will Likely Acquire Another Hypertension Therapy Firm, Medcity News, Apr. 27, 2012; 3:06 p.m.; medcitynews.com.
Medtronic, Inc., RDN Therapy with the Symplicity Renal Denervation System, Procedure Fact Sheet, www.medtronic.com, 2011.
Ardian, Inc., Ardian(R) Receives 2010 EuroPCR Innovation Award and Demonstrates Further Durability of Renal Denervation Treatment for Hypertension, PR Newswire, Jun. 3, 2010.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Oz, Mehmet, Pressure Relief, TIME Magazine, Monday, Jan. 9, 2012.

* cited by examiner

CATHETER SYSTEM AND ELECTRODE ASSEMBLY FOR INTRAPROCEDURAL EVALUATION OF RENAL DENERVATION

CROSS-REFERENCE TO RELATED APPLICATIONS

This application claims the benefit of U.S. Provisional Patent Application No. 62/353,606, filed Jun. 23, 2016, the contents of which are hereby incorporated by reference herein in their entirety.

A. FIELD OF THE DISCLOSURE

The present disclosure relates generally to catheter systems and methods for the intraprocedural evaluation of a renal denervation procedure. In particular, the present disclosure relates to a catheter system that includes an electrode assembly that has at least one electrically insulated spline that is interconnected with an electrical wire to allow the at least one spline to function as a stimulation electrode. The electrically active spline can provide electrical stimulation to the interior of the renal artery during a procedure to allow for operational feedback.

B. BACKGROUND

Hypertension remains the most prevalent cardiovascular risk factor around the globe today. In humans, sympathetic nerve activity is increased in almost all forms of hypertension. Various renal denervation ablation procedures for the ablation of perivascular renal nerves in the renal arteries have been used for the treatment of hypertension, and specifically for drug-resistant hypertension. Generally, one or more radiofrequency electrodes are introduced into the body and fed into the renal artery and used to ablate the efferent and afferent nerves that generally run the length of the artery. In some cases, a single ablation procedure may include six to ten or more ablation areas along and around the wall of the artery. Typically, the operator performing the procedure will ablate one discrete area of the artery and then move the ablation electrode a desired distance lengthwise about the length of the artery and also rotate the handle of the catheter to move the ablation electrode circumferentially around the artery. In some cases, the operator may move the ablation electrode circumferentially about 45 degrees around the artery wall between ablations. By varying the ablation treatment sites lengthwise down and circumferentially around the artery wall, any potential overall damage to the artery wall can be minimized or eliminated while the overall ablation of the efferent and afferent nerves can still be substantially complete and effective.

During the ablation procedure, the operator, typically a doctor, performing the procedure generally attempts to monitor and track all of the areas of the artery wall that have previously been ablated to avoid over-treatment of any one site. This monitoring and tracking is generally done both along the length of the artery as well as around the circumference of the artery wall to ensure proper ablation of the arterial nerves and the best procedural results. Feedback to the operator is generally provided regarding the temperature at the ablation site, which can also be indicative of the effectiveness of the ablation procedure itself, and whether the nerve has been ablated to a desired point.

BRIEF SUMMARY OF THE DISCLOSURE

The present disclosure provides catheter systems, electrode assemblies, and methods for electrically stimulating one or more points about the circumference of the renal artery to provide real time intraprocedural operational feedback to the operator of a renal denervation procedure to allow for more precise and thorough ablation of the renal artery and better patient outcomes. In many embodiments, an electrode assembly is provided that includes multiple splines that extend from an insulated proximal hub to an insulated distal hub and are interconnected to an electrical wire to allow the splines to independently function as electrical stimulation electrodes. The electrically active splines can then be energized at one or more desired points during a renal denervation procedure to provide electrical stimulation to the renal artery and operational feedback to the operator. Various embodiments of the present disclosure are set forth herein.

In one embodiment, the present disclosure is directed to a catheter system. The catheter system comprises: (i) a catheter shaft; and (ii) an electrode assembly carried by the catheter shaft and including a proximal hub, a distal hub, and a first spline extending from the proximal hub to the distal hub, wherein the first spline includes a first ablation electrode thereon. The first spline is interconnected with an electrical wire to allow the first spline to function as a stimulation electrode.

In another embodiment, the present disclosure is directed to an electrode assembly. The electrode assembly comprises: (i) an electrically insulating proximal hub and an electrically insulating distal hub; (ii) a first spline extending from the electrically insulating proximal hub to the electrically insulating distal hub and carrying a first ablation electrode; and (iii) a second spline extending from the electrically insulating proximal hub to the electrically insulating distal hub and carrying a second ablation electrode. The first spline and the second spline are interconnected with an electrical wire to allow the first spline and the second spline to independently function as stimulation electrodes.

In another embodiment, the present disclosure is directed to a method of evaluating the intraprocedural success of a renal denervation procedure on a subject. The method comprises: (i) electrically stimulating multiple points about the circumference of a renal artery of the subject using at least one spline of an electrode assembly as a stimulation electrode to determine a baseline physiological response of the subject; (ii) performing a renal denervation procedure on the renal artery of the subject; (iii) electrically stimulating the multiple points about the circumference of the renal artery of the subject using at least one spline of an electrode assembly as a stimulation electrode to determine the physiological response of the subject; and (iv) comparing the baseline physiological response of the subject prior to renal denervation with the physiological response after renal denervation.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
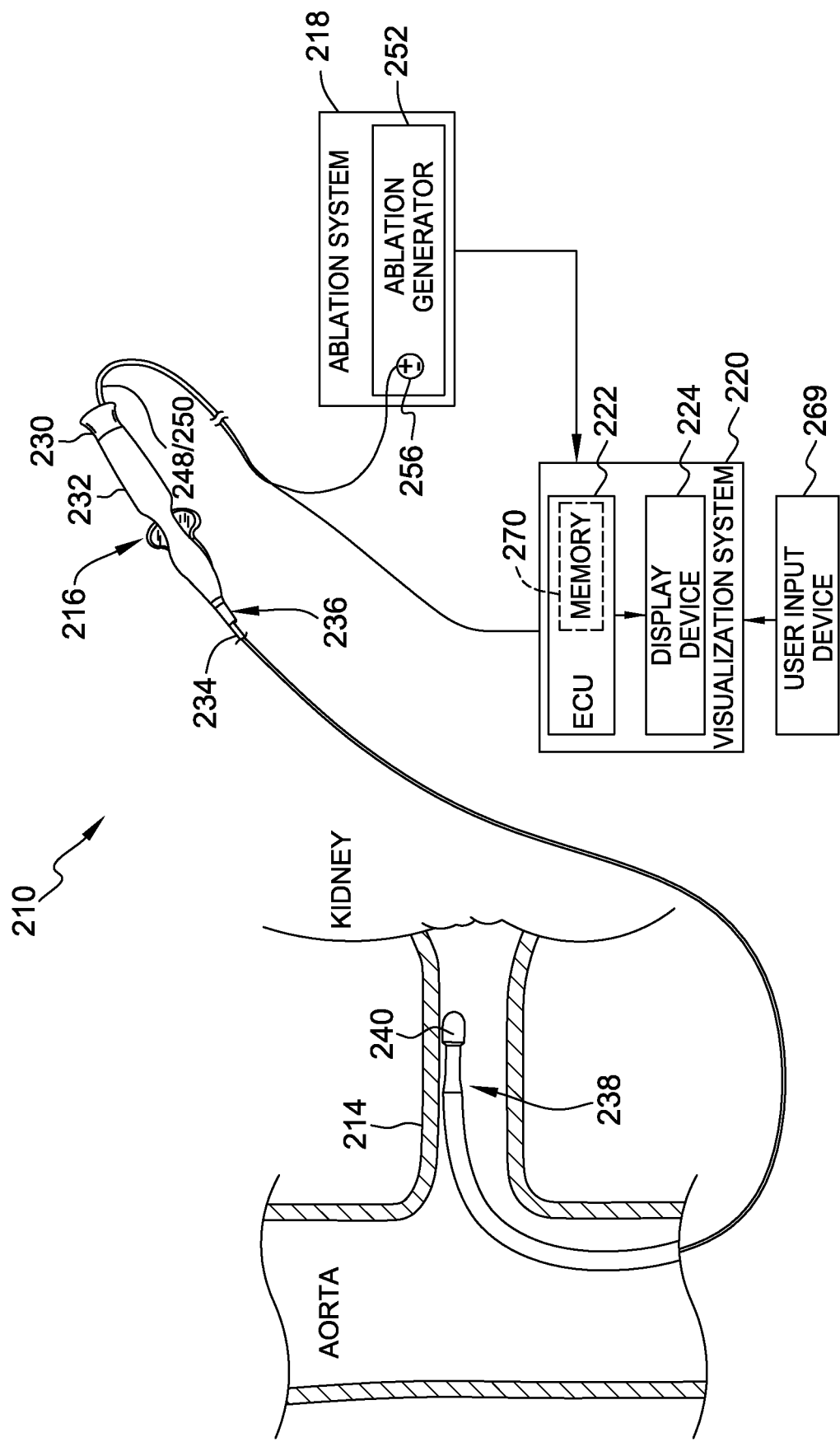
FIG. 1 is a diagrammatic view of a renal denervation system for presenting information relating to lesion formation in a renal artery.

The present disclosure provides catheter systems and electrode assemblies for use in methods for providing real time feedback to an operator, such as a doctor, performing a renal denervation procedure on a subject. These catheter systems and electrode assemblies provide at least one, and in many embodiments two, three, four or more, electrically active splines that can be used to electrically stimulate the interior of the renal artery. The electrically active splines may also carry one or more ablation electrodes, thermocouples, or other electronic devices. By making one or more splines on the electrode basket electrically active, there is no need in many embodiments to provide additional electrical stimulation electrodes on the one of more splines to provide this functionality. The electrically active splines may be configured to operate independently of one another, and are generally secured to a proximal insulated hub and a distal insulated hub in the electrode assembly to allow the electrically active spline to be electrically insulated and electrically isolated.

In many embodiments, methods are provided for evaluating the intraprocedural confirmation of the end point of a renal denervation procedure such that the operator can assess the effectiveness of a procedure and decide whether additional renal denervation may be beneficial to the subject. Methods are also provided for screening subjects to determine whether the subject might benefit from a renal denervation procedure. The methods of the present disclosure utilize a modified ablation catheter including an electrode assembly having one or more electrically active splines in combination with ablation electrodes for electrical stimulation of multiple points about the circumference of the renal artery to provide intraprocedural feedback to the operator. In many embodiments, the multiple points about the circumference of the renal artery will include at least one point in each of the four quadrants of the renal artery. As used herein, "quadrant" refers to a circular section equal to one quarter of a circle such that the renal artery, which is generally circular in cross-section, would include four quadrants.

More specifically, many embodiments of the present disclosure utilize electrically active splines of an electrode basket to provide simultaneous or sequential electrical stimulation of multiple points about the circumference of the renal artery, or section thereof, prior to a renal denervation procedure to establish a baseline physiological response (such as a baseline blood pressure, baseline heart rate, baseline renal blood flow, or other physiological response as described herein) of a subject prior to any renal denervation taking place in the renal artery. By using electrical stimulation of multiple points about the circumference of the renal artery, the physiological response is amplified due to the cumulative response of the multiple-point electrical stimulation as further described herein. The present methods significantly increase the likelihood of obtaining the true and accurate physiological response due to the electrical stimulation of multiple points about the circumference of the renal artery. Once the baseline physiological response has been established after electrical stimulation, the operator can perform a renal denervation procedure on the renal artery and then subsequently electrically stimulate the multiple points about the circumference of the renal artery again with the electrically active spline or splines of the electrode assembly to measure the physiological response of the subject after the renal denervation is complete. With this information, the operator can compare the physiological response before the renal denervation (after the first electrical stimulation) with the physiological response after renal denervation (after the second electrical stimulation), and determine, intraprocedurally, the effectiveness of the procedure and whether the subject may benefit from further denervation. The operator can also minimize both the number of ablations performed and the energy used, which can reduce or eliminate any potential damage to the renal artery and improve patient outcomes. Additionally, the real time information may allow for improved overall procedure management and efficiency. The methods of the present disclosure may further be utilized to screen potential renal denervation subjects to segregate those that might benefit from a renal denervation procedure from those that likely would not benefit.

The efferent and afferent nerves that lie within and immediately adjacent to the wall of the renal artery propagate longitudinally down the length of the renal wall in a non-uniform pattern that may be sometimes described as a spider-web or variable and non-predictable pattern. As such, it is generally difficult to determine the exact position of the efferent and afferent nerves of the renal artery. The methods of the present disclosure account for this irregular and unpredictable longitudinal propagation of the efferent and afferent nerves through the electrical stimulation of multiple points about the circumference of the renal artery using electrically active electrode basket splines as described herein to elucidate the desired physiological response at the desired time of the procedure. By electrically stimulating at multiple points about the circumference of the renal artery using the electrically active splines, the ability to achieve sufficient electrical stimulation of the efferent and afferent nerves, and thus elicit a significant and measurable impact on the desired physiological response being evaluated, is significantly increased. The multiple point electrical stimulation results in a substantially increased likelihood of the electrical stimulation interacting with the desired nerves as a greater area of the renal artery is electrically stimulated. In many embodiments, it is desirable to have electrical stimulation occur in at least one location in each of the four quadrants of the renal artery; that is, it is desirable in some embodiments to electrically stimulate at least one location in each of the four quadrants of the renal artery. In many embodiments, the electrical stimulation points about the circumference of the renal artery may be equally spaced apart to reduce the potential of any damage to the renal artery and/or the efferent and afferent nerves.

For purposes of this description, the methods, systems, and apparatuses of the present disclosure will be primarily described in connection with the use of an ablation catheter and electrode assembly having two or four splines, with each spline being electrically active such that it may provide electrical stimulation to the interior of the renal artery. Some or all of the electrically active splines may include an ablation electrode. It is contemplated, however, that numerous other types of ablation catheters and electrode assemblies, including electrode assemblies having 3, 5, 6, 7, 8, 9, 10 or more splines, some or all of which being electrically active as described herein, can be used in the methods of the present disclosure as would be appreciated by one of ordinary skill in the art based on the disclosure herein.

Referring now to the Figures, FIG. 1 illustrates one exemplary embodiment of a general ablation system 210 for performing one or more diagnostic and/or therapeutic functions that include components for presenting information representative of lesion formations in renal artery 214 during an ablation procedure performed thereon.

Among other components, system 210 includes a medical device (such as, for example, catheter 216), ablation system 218, and system 220 for the visualization, navigation, and/or mapping of internal body structures. System 220 may include, for example and without limitation, an electronic control unit (ECU) 222, display device 224, user input device 269, and memory 270. Alternatively, ECU 222 and/or display device 224 may be separate and distinct from, but electrically connected to and configured for communication with, system 220.

With continued reference to FIG. 1, catheter 216 is provided for examination, diagnosis, and/or treatment of internal body tissues, such as renal artery 214. In an exemplary embodiment, catheter 216 comprises a radio frequency (RF) ablation catheter. It should be understood, however, that catheter 216 is not limited to an RF ablation catheter. Rather, in other embodiments, catheter 216 may comprise an irrigated catheter and/or other types of ablation catheters (e.g., cryoablation, ultrasound, etc.).

In an exemplary embodiment, catheter 216 is electrically connected to ablation system 218 to allow for the delivery of RF energy. Catheter 216 may include a cable connector or interface 230, handle 232, shaft 234 having a proximal end 236 and distal end 238 (as used herein, "proximal" refers to a direction toward the end of catheter 216 near the operator, and "distal" refers to a direction away from the operator and (generally) inside the body of a subject or patient), and one or more electrodes 240 mounted in or on shaft 234 of catheter 216. In an exemplary embodiment, electrode 240 is disposed at or near distal end 238 of shaft 234, with electrode 240 comprising an ablation electrode disposed at the extreme distal end 238 of shaft 234 for contact with renal artery 214. Catheter 216 may further include other conventional components such as, for example and without limitation, sensors, additional electrodes (e.g., ring electrodes) and corresponding conductors or leads, or additional ablation elements, e.g., a high intensity focused ultrasound ablation element and the like.

Connector 230 provides mechanical and electrical connection(s) for cables 248 and 250 extending from ablation system 218, and visualization, navigation, and/or mapping system 220. Connector 230 is conventional in the art and is disposed at the proximal end of catheter 216.

Handle 232 provides a location for the operator to hold catheter 216 and may further provide means for steering or guiding shaft 234 within renal artery 214. For example, handle 232 may include means to change the length of a guidewire extending through catheter 216 to distal end 238 of shaft 234 to steer shaft 234. Handle 232 is also conventional in the art and it will be understood that the construction of handle 232 may vary. In another exemplary embodiment, catheter 216 may be robotically driven or controlled. Accordingly, rather than an operator manipulating a handle to steer or guide catheter 216, and shaft 234 thereof, in particular, a robot is used to manipulate catheter 216.

Shaft 234 is generally an elongated, tubular, flexible member configured for movement within renal artery 214. Shaft 234 supports, for example and without limitation, electrode 240, associated conductors, and possibly additional electronics used for signal processing or conditioning. Shaft 234 may also permit transport, delivery and/or removal of fluids (including irrigation fluids, cryogenic ablation fluids, and bodily fluids), medicines, and/or surgical tools or instruments. Shaft 234 may be made from conventional materials such as polyurethane, and defines one or more lumens configured to house and/or transport at least electrical conductors, fluids, or surgical tools. Shaft 234 may be introduced into renal artery 214 through a conventional introducer. Shaft 234 may then be steered or guided through renal artery 214 to a desired location with guidewires or other means known in the art.

With further reference to FIG. 1, ablation system 218 is comprised of, for example, ablation generator 252. Ablation generator 252 generates, delivers, and controls RF energy output by ablation catheter 216 and electrode 240 thereof, in particular. In an exemplary embodiment, generator 252 includes RF ablation signal source 256 configured to generate an ablation signal that is output across a pair of source connectors: a positive polarity connector SOURCE (+), which may be electrically connected to tip electrode 240 of catheter 216; and a negative polarity connector SOURCE (−). It should be understood that the term connectors as used herein does not imply a particular type of physical interface mechanism, but is rather broadly contemplated to represent one or more electrical nodes. Source 256 is configured to generate a signal at a predetermined frequency in accordance with one or more user specified parameters (e.g., power, time, etc.) and under the control of various feedback sensing and control circuitry as is known in the art. Source 256 may generate a signal, for example, with a frequency of about 450 kHz or greater. Generator 252 may also monitor various parameters associated with the ablation procedure including, for example, impedance, the temperature at the distal tip of the catheter, applied ablation energy, and the position of the catheter, and provide feedback to the clinician or another component within system 210 regarding these parameters.

In accordance with the present disclosure, ablation catheters suitable for use in the processes and systems described herein for the evaluation of the intraprocedural success of a renal denervation procedure and/or patient screening include an electrode assembly wherein one or more of the splines are electrically active; that is, wherein one or more of the splines of the electrode assembly are electrically insulated and isolated and are capable of providing electrical stimulation to the interior of the renal artery independent of any other component. The electrically active splines will also in many embodiments each also include at least one ablation electrode thereon, and may optionally include a thermocouple and/or other sensors or electronic devices. The exact type and design of the ablation catheter and electrode basket is not critical so long as the ablation catheter and electrode basket is configured to allow for at least one spline to be electrically active so as to provide electrical stimulation at about the circumference of the renal artery. In some embodiments, the ablation catheter is sized and configured with electrically active splines to allow for electrical stimulation of at least 2, or even 3, or even 4 or even 5 or even 6 or even 7 or even 8 or more points about the circumference of the renal artery. In many embodiments, the ablation catheter is sized and configured such that the electrical stimulation at multiple points is generally equally spaced apart about the circumference of the renal artery. In one specific embodiment, the ablation catheter is sized and configured to allow for electrical stimulation at one point within each of the four quadrants of the renal artery. Such four quadrant electrical stimulation may desirably be equally spaced apart in many embodiments. Many types of ablation catheters may be configured in this manner and are suitable for use in accordance with the present disclosure including, for example, multiple spline catheters (i.e., electrode baskets having 2, 3, 4, 5, 6, or more splines), spiral catheters, balloon catheters, and the like).

Figure 2:
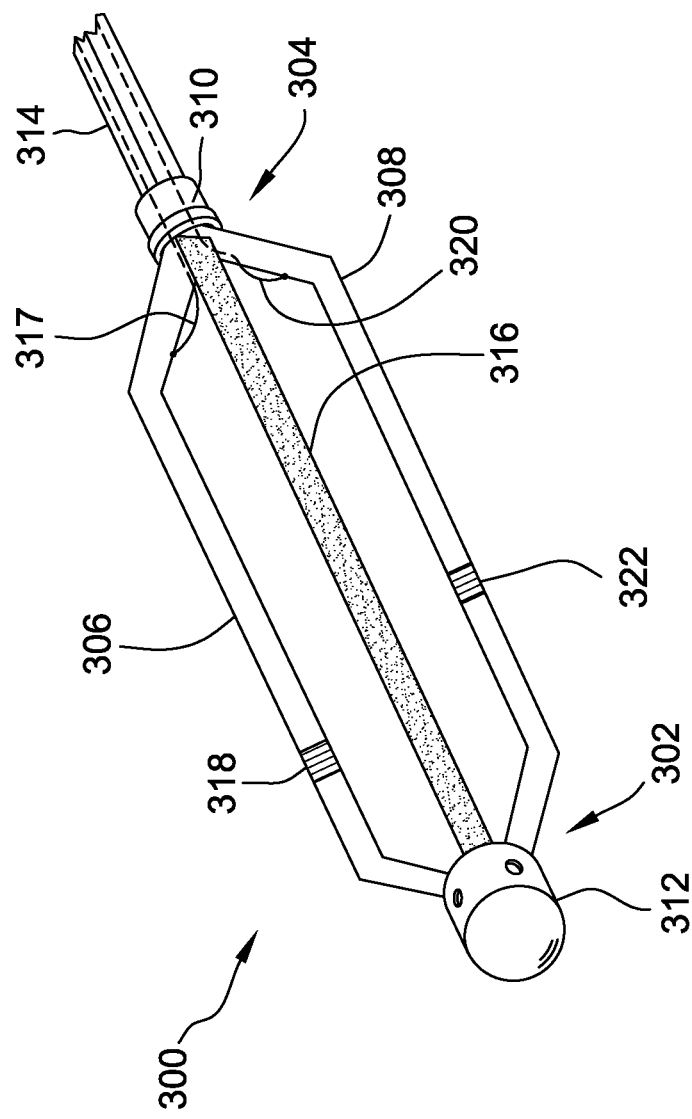
FIG. 2 is a diagram of an electrode basket including two electrically active splines suitable for use in the present processes.

Referring now to FIG. 2, there is illustrated an electrode basket in accordance with one embodiment of the present disclosure that is suitable for use with an ablation catheter in the methods of the present disclosure. Electrode basket 300 has a distal end 302 and a proximal end 304 and includes electrically active spline 306 and electrically active spline 308. Electrically active splines 306 and 308 are connected to a proximal insulated hub 310 and a distal insulated hub 312 in order to electrically insulate and isolate electrically active splines 306 and 308. Proximal insulated hub 310 and distal insulated hub 312 may be constructed from any suitable electrically insulating material including, for example, polymeric materials and thermoplastic materials including Ultem™ or another polyetherimide. Other high temperature liquid crystal polymers are also suitable for use in the construction of proximal insulated hub 310 and distal insulated hub 312. Electrode basket 300 also includes elongated catheter body 314 through which pulling wire 316 runs through and connects to distal insulated hub 312. Pulling wire 316 can be used to expand/contract electrode basket 300 into different conformations before, during, and after an ablation procedure. Also running through elongated catheter body 314 is electrical wire 317 which is electrically connected to electrically active spline 306 and electrical wire 320 which is electrically connected to electrically active spline 308. Electrical wire 317 and electrical wire 320 are connected to an electrical source (not shown) such that they can carry electricity to electrically active spline 306 and electrically active spline 308 such that electrically active spline 306 and electrically active spline 308 are electrically active and capable of providing electrical stimulation as described herein.

With continued reference to FIG. 2, electrically active spline 306 and electrically active spline 308 of electrode basket 300 each include ablation electrode 318 and 322, respectively. Ablation electrodes 318 and 322 are positioned on electrically active spline 306 and electrically active spline 308, respectfully to allow contact thereof with different quadrants of a renal artery (not shown in FIG. 2 but see FIG. 1) after insertion and expansion therein. Each of ablation electrodes 318 and 322 are electrically insulated (electrical insulation not shown in FIG. 2) from electrically active spline 306 and electrically active spline 308 to ensure that each electrical component can act independently and without short circuits or other electrical interference problems. In many embodiments, the same material of construction may be used for electrically active splines 306 and 308 and for ablation electrodes 318 and 322. Suitable materials may include, for example, gold and alloys thereof, platinum and alloys thereof, stainless steel and alloys thereof, and metal alloys of nickel and titanium and combinations thereof.

Figure 3:
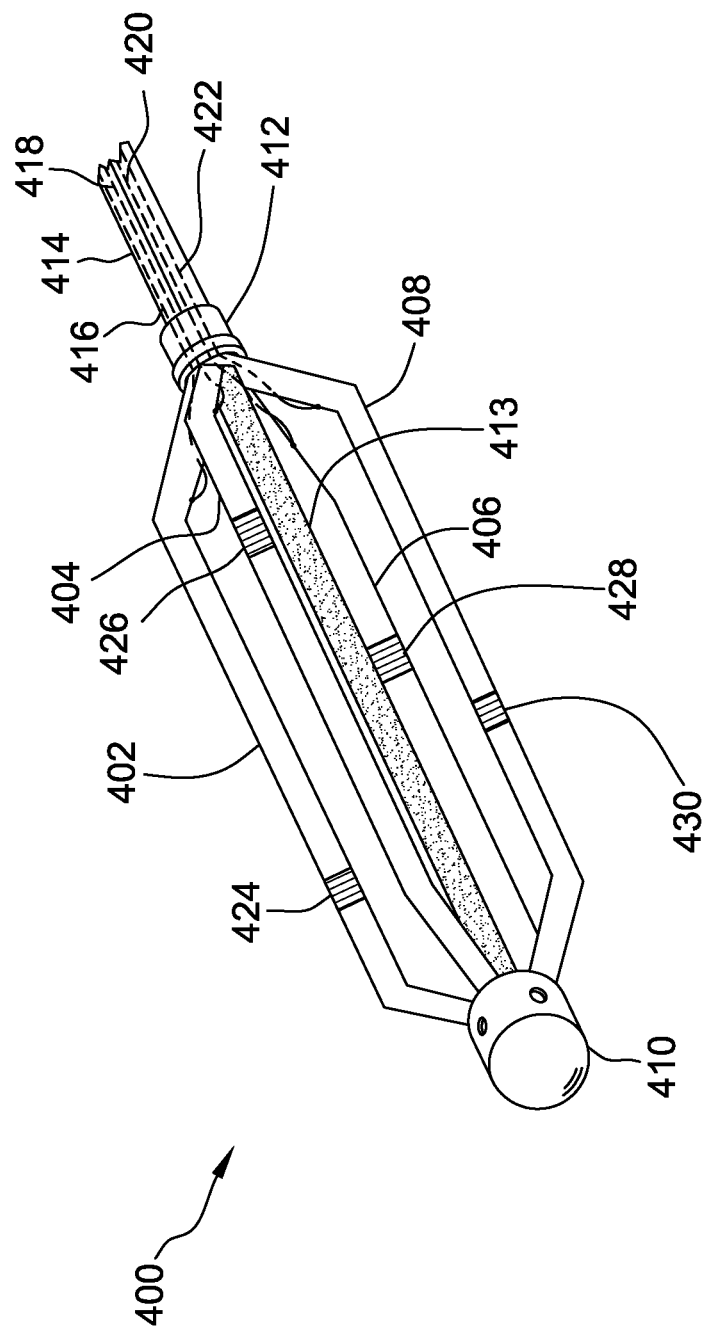
FIG. 3 is a diagram of an electrode basket including four electrically active splines suitable for use in the present processes.

Referring now to FIG. 3, there is illustrated an electrode basket in accordance with one embodiment of the present disclosure that is suitable for use with an ablation catheter in methods of the present disclosure. Electrode basket 400 includes four electrically active splines 402, 404, 406, and 408 each connected to distal insulated hub 410 and proximal insulated hub 412. Electrode basket 400 also includes elongated catheter body 414 through which pulling wire 413 runs through and connects to distal insulated hub 410. Pulling wire 413 can be used to expand/contract electrode basket 400 into different conformations before, during, and after an ablation procedure. Also running through elongated catheter body 414 is electrical wire 416 which is electrically connected to electrically active spline 402, electrical wire 418 which is electrically connected to electrically active spline 404, electrical wire 420 which is electrically connected to electrically active spline 406 and electrical wire 422 which is electrically connected to electrically active spline 408. Electrical wire 416, electrical wire 418, electrical wire 420, and electrical wire 422 are each connected to an electrical source (not shown) such that they can carry electricity to electrically active spline 402, electrically active spline 404, electrically active spline 406, and electrically active spline 408 such that electrically active spline 402, electrically active spline 404, electrically active spline 406 and electrically active spline 408 are electrically active and capable of providing electrical stimulation as described herein. Although illustrated in FIG. 3 as four separate electrical wires, it will be recognized by one skilled in the art based on the disclosure herein that other electrical configurations, such as a single wire attached to all four electrically active splines, are within the scope of the present disclosure.

With continued reference to FIG. 3, electrically active spline 402, electrically active spline 404, electrically active spline 406, and electrically active spline 408 of electrode basket 400 each include ablation electrode 424, 426, 428, and 430, respectively. Ablation electrodes 424, 426, 428, and 430 are positioned on electrically active spline 402, electrically active spline 404, electrically active spline 406, and electrically active spline 408 to allow contact thereof with each quadrant of a renal artery (not shown in FIG. 3 but see FIG. 1) after insertion and expansion therein. Each of ablation electrodes 424, 426, 428, and 430 are electrically insulated (electrical insulation not shown in FIG. 3) from electrically active spline 402, electrically active spline 404, electrically active spline 406, and electrically active spline 408 to ensure that each electrical component can act independently and without short circuits or other electrical interference problems.

In accordance with many embodiments of the present disclosure, a single electrically active spline on an electrode basket may be used with the ablation electrode mounted thereon as a bipolar pair for electrical stimulation of the interior of the renal artery. In other embodiments, two adjacent, or two opposed, electrically active splines may be used as a bipolar pair for spline to spline electrical stimulation of the interior of the renal artery. In other embodiments, one or more electrically active splines can be coupled to a body patch and used as a bipolar pair for electrical stimulation of the interior of the renal artery. In many embodiments, the one or more pairs of electrically active splines are sequentially stimulated, although simultaneous stimulation is within the scope of the present disclosure as discussed herein.

In one exemplary embodiment of the present disclosure, the bipolar electrical stimulation to the interior of the renal artery is provided through sequential electrical stimulation of electrically active splines 402 and 406 followed by electrically active splines 404 and 408, followed by electrically active splines 402 and 406, and followed by electrically active spline 404 and 408, etc. Other bipolar sequential stimulation patterns are also within the scope of the present disclosure.

In some embodiments of the present disclosure, the electrically active splines as described herein are configured such that the entire spline may act as an electrical stimulation electrode; that is, the spline is configured such that the entire length of the spline is electrically active. In other embodiments of the present disclosure, the spline may be configured such that only a portion, or portions, of the spline is capable of functioning as an electrical stimulation electrode. In these embodiments, the spline may include one or more areas that are electrically isolated or insulated such that these areas do not conduct electricity and cannot function as an electrical stimulation site. In some embodiments, only one quarter, or one half, or even only three quarters of the length of the spline will be electrically active, with the remaining lengthwise portions being electrically insulated or isolated.

As discussed in further detail herein, the electrical stimulation provided by the one or more electrically active splines as described herein is desirably at an intensity level sufficient to elicit the desired physiological response in the subject, but is not too intense as to potentially damage the renal artery or nerves therein or introduce a high level of pain to the subject; that is, the electrical stimulation provided by the one or more electrically active splines to the multiple points about the circumference of the renal artery should not be too diffuse or too intense.

In accordance with various embodiments of the present disclosure, ablation catheters including electrode assemblies having one or more splines capable of providing electrical stimulation may be used in methods described herein for the evaluation of the intraprocedural success of a renal denervation procedure on a subject; that is, electrical stimulation to the renal artery at prescribed times as described herein may be used to provide real time feedback to the operator of a renal denervation procedure on a subject to allow the operator to determine how successful a renal denervation procedure on the subject has been, and determine whether further denervation may be beneficial or desirable. Other embodiments allow for methods of screening patients for renal denervation procedures. A number of exemplary methods of the present disclosure are set forth in FIGS. 4-7 and described in more detail hereinbelow.

Figure 4:
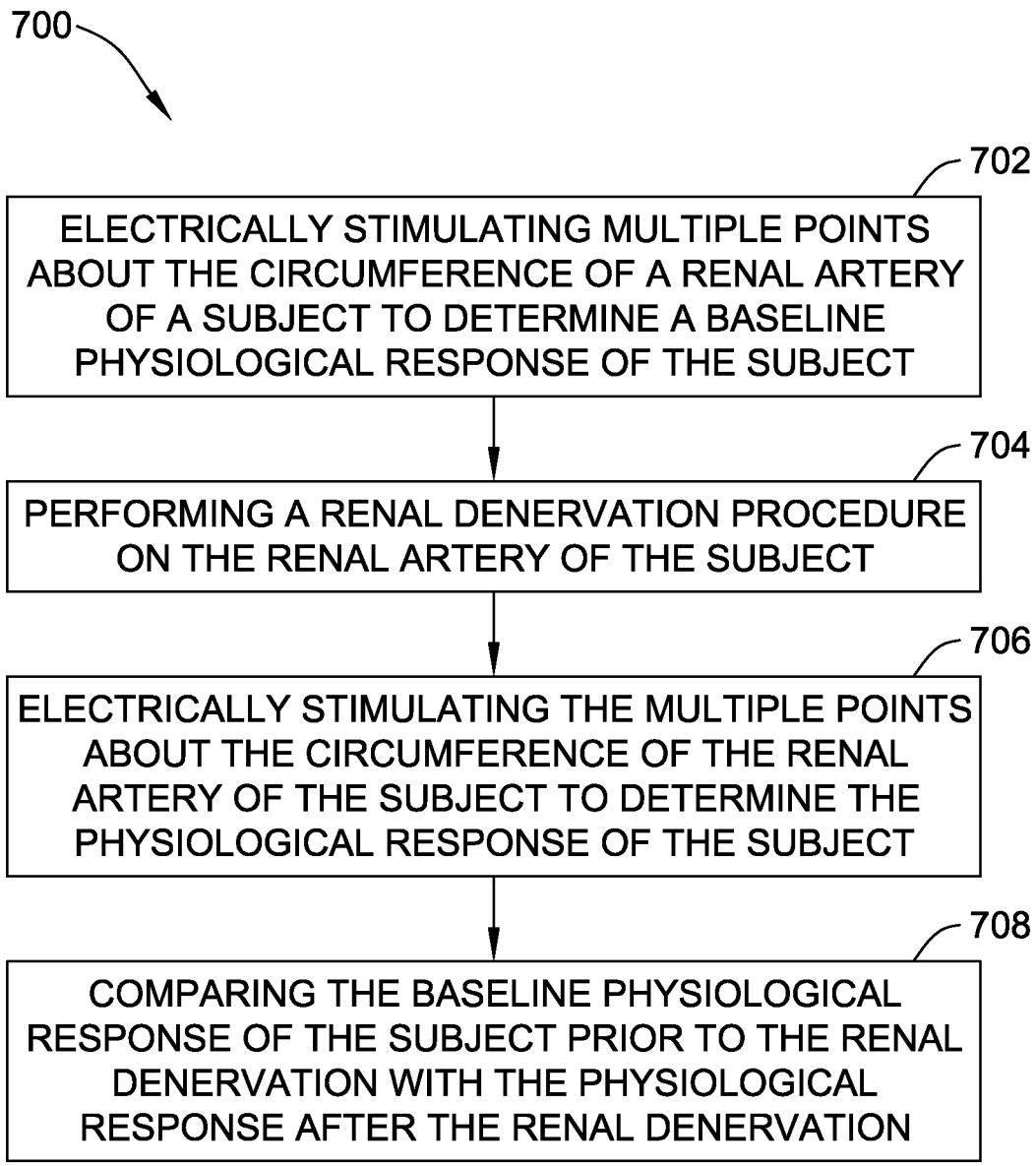
FIG. 4 is a flow chart of one embodiment of a method for evaluating the intraprocedural success of a renal denervation procedure on a subject.

FIG. 4 is a flow chart of one embodiment of a method 700 for evaluating the intraprocedural success of a renal denervation procedure. Method 700 includes electrically stimulating 702 multiple points about the circumference of a renal artery of a subject to determine a baseline physiological response of the subject; performing 704 a renal denervation procedure on the renal artery of the subject; electrically stimulating 706 the multiple points about the circumference of the renal artery of the subject to determine the physiological response of the subject; and comparing 708 the baseline physiological response of the subject prior to the renal denervation with the physiological response after the renal denervation.

Figure 5:
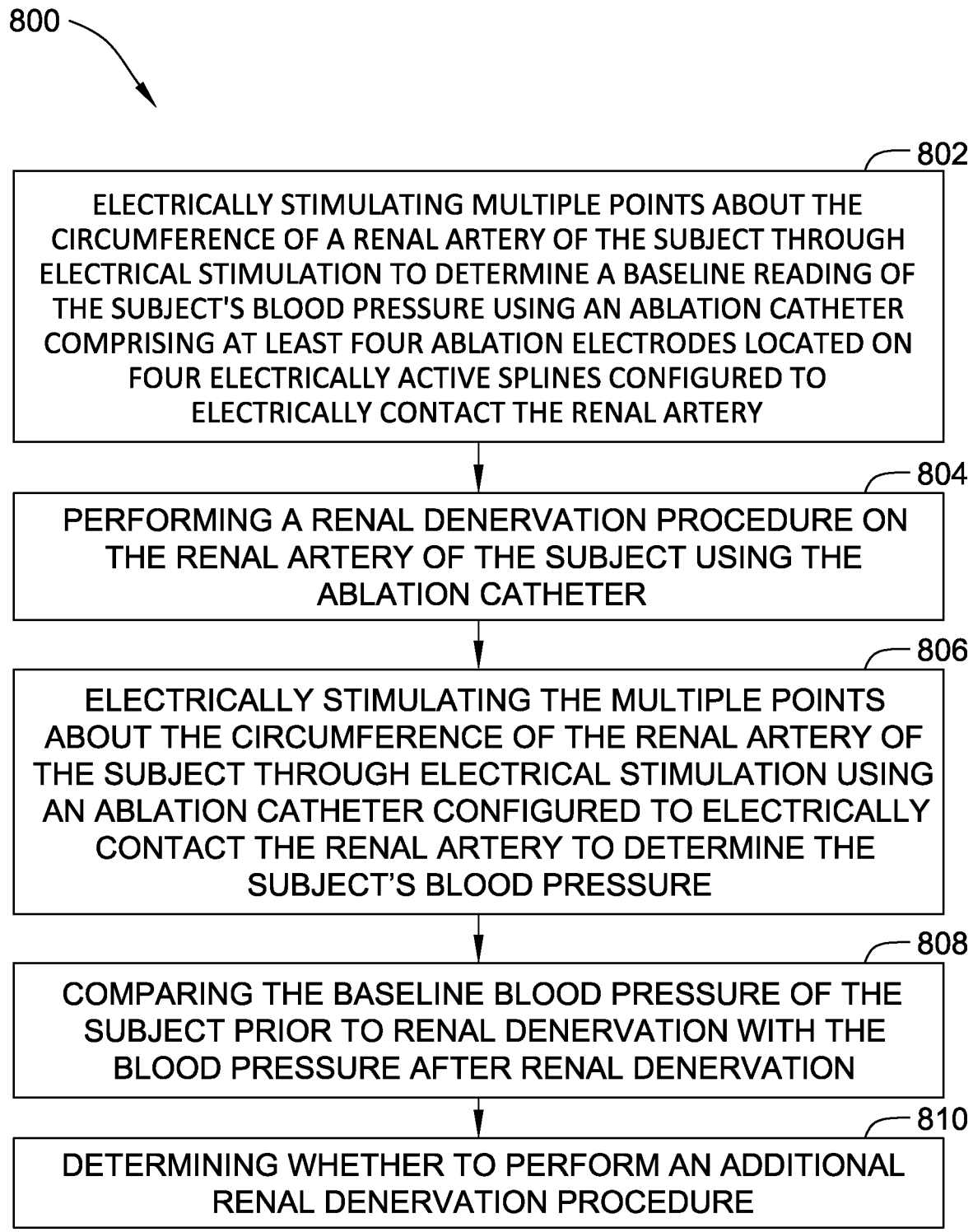
FIG. 5 is a flow chart of one embodiment of a method of determining the end point of a renal denervation procedure on a subject.

FIG. 5 is a flow chart of one embodiment of a method 800 for determining the end point of a renal denervation procedure on a subject. Method 800 includes electrically stimulating 802 multiple points about the circumference of a renal artery of the subject through electrical stimulation to determine a baseline reading of the subject's blood pressure using an ablation catheter comprising at least four ablation electrodes located on four electrically active splines configured to electrically contact the renal artery; performing 804 a renal denervation procedure on the renal artery of the subject using the ablation catheter; electrically stimulating 806 the multiple points about the circumference of the renal artery of the subject through electrical stimulation using an ablation catheter configured to electrically contact the renal artery to determine the subject's blood pressure; comparing 808 the baseline blood pressure of the subject prior to renal denervation with the blood pressure after renal denervation; and determining 810 whether to perform an additional renal denervation procedure.

Figure 6:
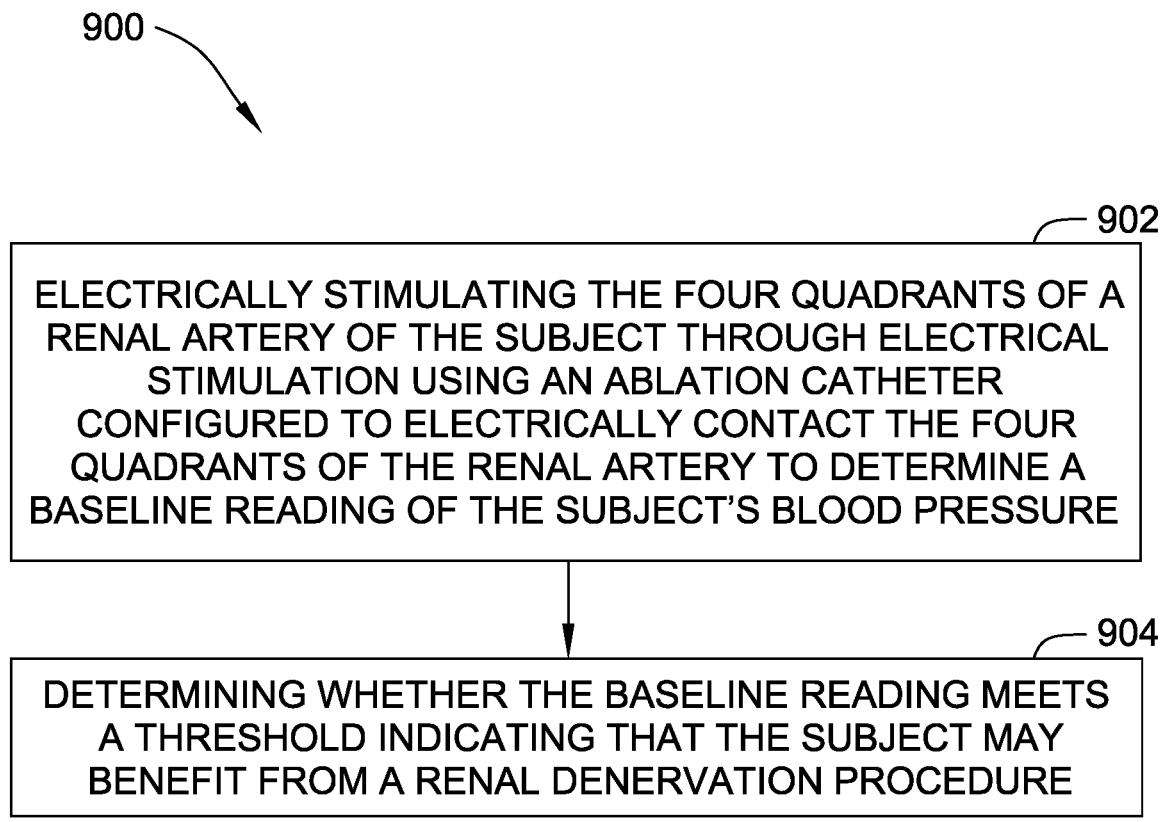
FIG. 6 is flow chart of one embodiment of a method of screening a subject for a renal denervation procedure.

FIG. 6 is a flow chart of one embodiment of a method 900 of screening a subject for a renal denervation procedure. Method 900 includes electrically stimulating 902 the four quadrants of a renal artery of the subject through electrical stimulation using an ablation catheter configured to electrically contact the four quadrants of the renal artery to determine a baseline reading of the subject's blood pressure and determining 904 whether the baseline reading meets a threshold indicating that the subject may benefit from a renal denervation procedure.

Figure 7:
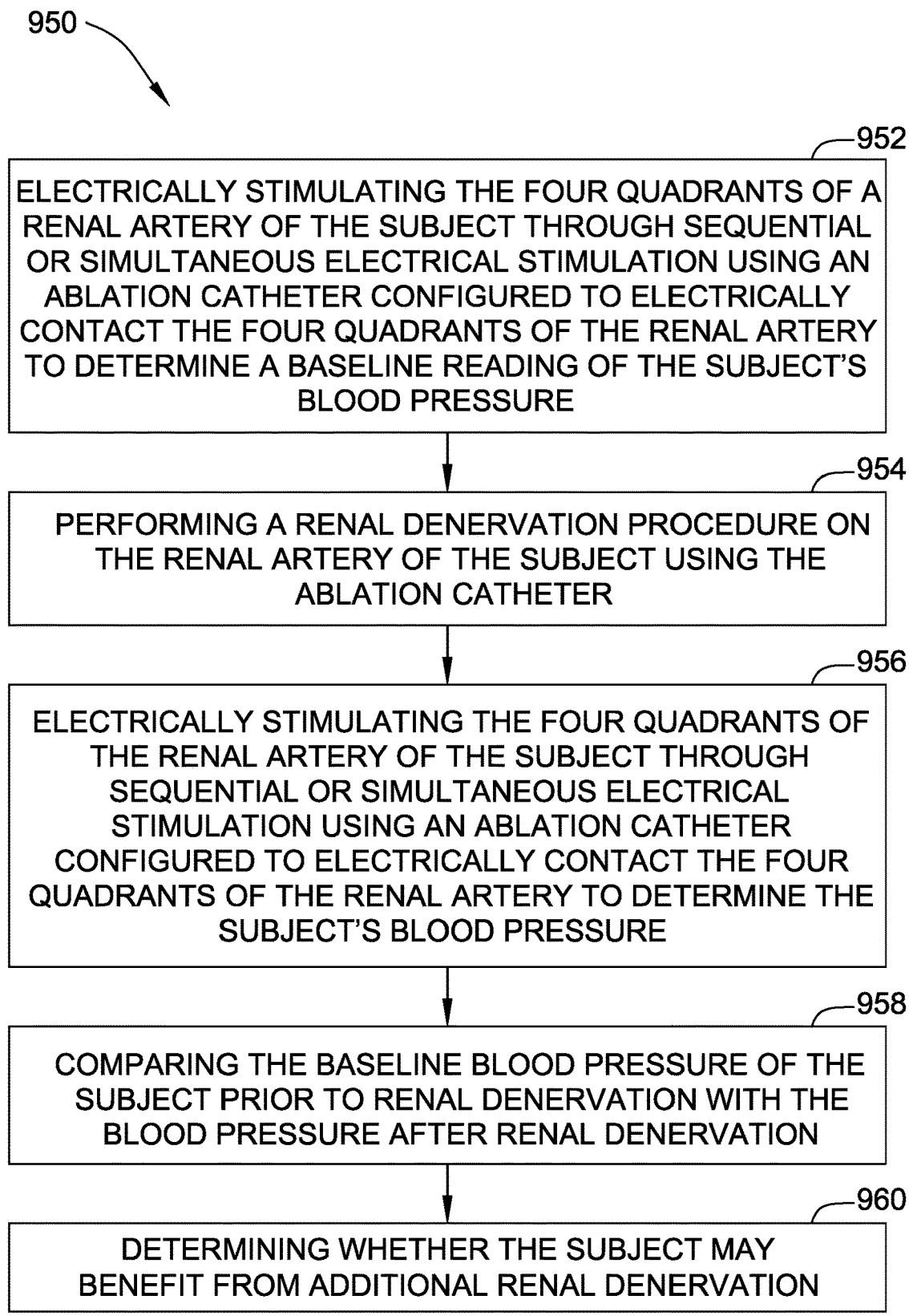
FIG. 7 is a flow chart of another embodiment of a method of screening a subject for a renal denervation procedure.

FIG. 7 is a flow chart of one embodiment of a method 950 of screening a subject for a renal denervation procedure. Method 950 includes electrically stimulating 952 the four quadrants of a renal artery of the subject through sequential or simultaneous electrical stimulation using an ablation catheter configured to electrically contact the four quadrants of the renal artery to determine a baseline reading of the subject's blood pressure; performing 954 a renal denervation procedure on the renal artery of the subject using the ablation catheter; electrically stimulating 956 the four quadrants of the renal artery of the subject through sequential or simultaneous electrical stimulation using an ablation catheter configured to electrically contact the four quadrants of the renal artery to determine the subject's blood pressure; comparing 958 the baseline blood pressure of the subject prior to renal denervation with the blood pressure after renal denervation; and determining 960 whether the subject may benefit from additional renal denervation.

In order to evaluate the intraprocedural success of a renal denervation procedure and/or perform patient screening, a baseline physiological response of the subject is first measured and recorded prior to any renal denervation occurring on the subject. A "baseline physiological response" refers to the response elicited by a subject after electrical stimulation of the multiple points about the circumference of the renal artery; for example, a baseline blood pressure would be the blood pressure determined after electrical stimulation. A number of physiological responses may be selected for measuring prior to the renal denervation procedure to establish a baseline reading that is later compared against another reading after renal denervation as described herein. Further examples include blood pressure, heart rate, renal blood flow, catecholamine (epinephrine and norepinephrine) level, heart rate variability, natriuresis, and other biomarker levels, and combinations thereof. In many embodiments, blood pressure is a desired physiological response to measure as a baseline as it can easily be measured outside of the subject's body throughout the course of the procedure. As used herein, the term "blood pressure" encompasses systolic blood pressure, diastolic blood pressure and mean blood pressure. Any of systolic blood pressure, diastolic blood pressure and mean blood pressure may be suitably used as a physiological response in accordance with the present disclosure. In some embodiments, two or more physiological responses may be measured.

The baseline physiological response of the subject is measured by first electrically stimulating multiple points about the circumference of the renal artery (or parts thereof as discussed below) using one or more electrically active splines on the electrode assembly as described above. As noted, the electrical stimulation at the multiple points about the circumference of the renal artery may be equally spaced about the circumference of the renal artery to lessen any chance of damage to the artery and/or the nerves due to over-stimulation. The renal artery may be stimulated about its circumference at 2, 3, 4, 5, 6, 7, 8 or more points to increase the likelihood that the efferent and afferent nerves are sufficiently electrically stimulated so as to provide the desired physiological response. In one particular embodiment, the electrical stimulation using the electrically active electrode basket splines occurs at a single point within each of the four quadrants of the renal artery, such that there are four electrical stimulation points (corresponding to the four quadrants of the renal artery) about the circumference of the renal artery, that may be desirably equally spaced apart about the circumference.

The stimulation parameters for the electrical stimulation for the electrically active splines to set include the current, pulse width, and frequency. At a particular fixed setting, the stimulation as described herein is generally performed for a time period of from about 60 seconds to about 120 seconds. The current and pulse rate can be varied to bring about the desired physiological response from the patient. The methods of the present disclosure provide improved reliability and consistency due to the fact that multiple points about the circumference of the renal artery are electrically stimulated (either sequentially or simultaneously with the electrically active spline(s)) to elicit the desired physiological response. As discussed herein, by electrically stimulating multiple points about the circumference of the renal artery, there is a significantly increased confidence level that the desired afferent and/or efferent renal artery nerves are stimulated to elicit the desired physiological response.

There are numerous sites within the renal artery that are suitable for the electrical stimulation to occur. Suitable sites within the renal artery include, for example, unilateral sites, bilateral sites, the length of the renal artery, near the ostium, near the bifurcation, renal arterial branches distal to the bifurcation, intra-renal artery branches, and combinations thereof. Prior to stimulation, in some cases the doctor or operator may monitor the blood pressure of the patient over a period of time from about 60 seconds to 120 seconds so as to understand the blood pressure patterns and typical variation in blood pressure prior to electrical stimulation. In many cases, the more the baseline blood pressure rises as a result of the electrical stimulation, the more effective a renal denervation procedure may be for the patient as this in indicative of active nerve pathways in the renal artery.

In some embodiments, the electrical stimulation within the renal artery may be performed using sequential (multiplexing) electrical stimulation; that is, the electrical stimulation provided to the nerves may be sequential in nature wherein one electrically active spline is energized, followed by the second, then the third, then the fourth, etc. Also, as noted, the electrically active splines may be energized in pairs such that a first pair is energized followed by a second pair, etc. When sequential electrical stimulation is employed, the physiological response measured is the cumulative physiological response generated by the electrical stimulation in total as the sequential firing is done very quickly as described herein. In other embodiments, the electrical stimulation within the renal artery may be performed using simultaneous electrical stimulation wherein all electrically active splines are energized at the same time such that the electrical stimulation to all four quadrants of the artery is provided as the same time. In some embodiments as described herein, sequential (multiplexing) electrical stimulation may be desirable as this type of electrical stimulation may result in a reduced chance of over-stimulation of the nerves.

The electrical stimulation provided to the renal artery by the electrically active splines generally provides a current in an amount of from about 0.1 milliamps to about 40 milliamps, including from about 10 milliamps to about 25 milliamps. This electrical current is supplied at a frequency of from about 1 Hertz to about 50 Hertz, including from about 15 Hertz to about 20 Hertz. The electrical current is generally supplied for a time period of from about 1 millisecond to about 25 milliseconds, including from about 1 millisecond to about 5 milliseconds, including from about 1 millisecond to about 2 milliseconds. The time between electrical stimulations may be from about 1 millisecond to about 10 milliseconds. In some embodiments, the electrical stimulation provided to the subject may be monopolar in nature (monopolar mode) between the electrically active spline and an indifferent electrode patch placed on the subject during a renal denervation procedure. In other embodiments as noted above, the electrical stimulation provided to the subject may be bipolar in nature (bipolar mode) between the electrically active spline and the adjacent electrically active spline or between two electrically active splines. Because renal nerves generally traverse primarily longitudinally along the length of the renal artery, in many embodiments bipolar electrical stimulation may be desirable and effective in depolarizing the nerves.

The electrical stimulation described herein may be delivered to the subject as rectangular pulse waves, triangular pulse waves, sinusoidal pulse waves, Gaussian pulse waves, and combinations thereof. The electrical stimulation wave forms may include monophasic, charge balanced, and imbalanced biphasic, all of which may be delivered with our without delay. In some embodiments, it is desirable to provide the electrical stimulation in the form of rectangular pulse waves in a multiplexing manner from the pairs of electrically active splines.

Figure 8:
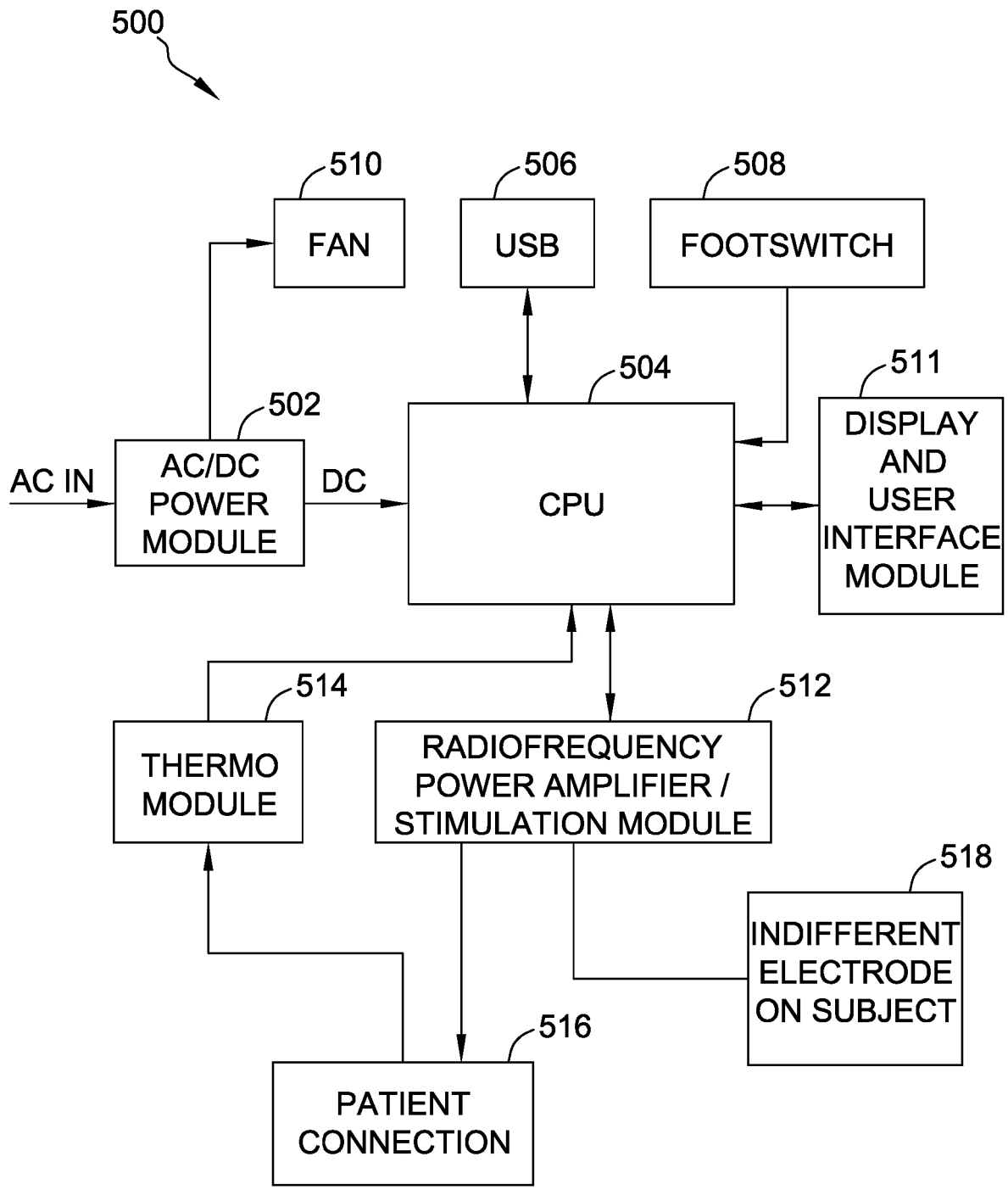
FIG. 8 is a block diagram of a radiofrequency ablation generator modified to include electrical stimulation.

In some embodiments of the present disclosure, it may be desirable to integrate the electrical stimulation functionality of the splines into the radiofrequency or ultrasound generator, or any other generator with an energy source, that is utilized to provide the ablation aspects of the renal denervation procedure so that only a single generator unit is required for the procedure. Referring now to FIG. 8, there is shown one exemplary radiofrequency ablation generator block diagram with an electrical stimulation module (for connection with the one or more electrically active splines) integrated therein. FIG. 8 illustrates the circuits in one embodiment that would allow the electrical stimulation functionality into a radiofrequency system. Specifically system 500 may include AC/DC power module 502 for accepting AC power in that provides DC power to a central processing unit (CPU) 504 that is in electrical communication with a USB port 506, Footswitch 508 and a display and user interface module 511. AC/DC power module 502 is also in communication with fan 510. Central processing unit 504 is further in electrical communication with a radiofrequency power amplifier/stimulation module 512 for supplying radiofrequency energy and electrical energy to the electrodes of an ablation catheter (not shown in FIG. 8), and thermo module 514. A patient connection 516 is in electrical contact with thermo module 514 and radiofrequency power amplifier/stimulation module 512. An indifferent electrode patch on the subject 518 is also in electrical communication with radiofrequency power amplifier/stimulation module. Of course, the electrical stimulation function as described herein may be provided to the subject in any number of other ways and methods in accordance with the present disclosure.

Once the baseline physiological response of the subject has been measured through the electrical stimulation of the multiple points about the circumference of the renal artery as described above and a sufficient time has passed to allow for the physiological response to return to normal (generally at least 1 minute, or 2 minutes, or 3 minutes, or 4 minutes or even 5 minutes), the operator may then perform the renal denervation procedure on the renal artery of the subject. In some cases, the operator may determine that the electrical stimulation of the renal artery did not elicit a suitable physiological response from the subject and may determine that the particular subject is not a good candidate of a renal denervation procedure; that is, the methods of the present disclosure may also allow an operator to screen subjects prior to the renal denervation procedure to determine whether the particular subject may benefit from the renal denervation procedure.

After the operator has completed the renal denervation procedure in the renal artery, the renal artery is then again electrically stimulated at multiple points about its circumference as described herein and the physiological response of the subject determined. Generally, it is desirable to provide the electrical stimulation after renal denervation in the same area where the electrical stimulation was provided to determine the baseline physiological response. It should be noted, however, that the stimulation after renal denervation could be made at a different location. The operator can then compare the baseline physiological response (that is, the physiological response generated by the subject prior to any renal denervation due to the electrical stimulation) to the physiological response generated after the renal denervation procedure and determine the effectiveness of the renal denervation procedure. This intraprocedural feedback then allows the operator to determine, in real time and based on the physiological responses of the subject, whether any additional renal denervation may benefit the subject or whether the procedure should be ended. In the event that the operator determines that additional renal denervation may benefit the subject, a further renal denervation procedure may be done and another subsequent physiological response based on electrical stimulation performed and again evaluated against the baseline physiological response. In some embodiments, it may be beneficial for a second renal denervation procedure to be performed if the blood pressure of the subject in response to the electrical stimulation has not been reduced by at least about 20%, or even at least about 30%, or even at least about 40%, or even at least about 50%, without causing hypotension. In many embodiments, a second renal denervation procedure may be desirable if the blood pressure on the subject in response to the electrical stimulation has not been reduced by at least about 10% after the first renal denervation procedure.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A catheter system comprising:
   a catheter shaft; and
   an electrode assembly carried by the catheter shaft and including:
   a proximal hub;
   a distal hub;
   a first spline extending between the proximal hub and the distal hub;
   a first ablation electrode positioned at a first axial location defined at a first distance between the proximal hub and the distal hub, wherein the first spline includes a proximal portion and a distal portion that are configured to be electrically activated together, and that are configured to be electrically activated independent of the first ablation electrode, and wherein the first ablation electrode is positioned on the first spline between the proximal portion and the distal portion of the first spline; and
   a second spline extending between the proximal hub and the distal hub, the second spline spaced circumferentially apart from the first spline, wherein the second spline includes a second ablation electrode positioned at a second axial location defined at a second distance between the proximal hub and the distal hub, the second axial location different from the first axial location, whereby the second ablation electrode is axially offset from the first ablation electrode, and whereby no ablation electrode of the electrode assembly is located in a same radial plane as any other ablation electrode of the electrode assembly,
   wherein the first spline is interconnected with a first electrical wire to allow the first spline to function as a first stimulation electrode,
   wherein the second spline is interconnected with a second electrical wire to allow the second spline to function as a second stimulation electrode, and wherein the first stimulation electrode and the second stimulation electrode are configured to elicit a physiological response capable of being measured when energized.

2. The catheter system of claim 1, wherein the proximal hub and the distal hub are constructed from an electrically insulating material.

3. The catheter system of claim 2, wherein the insulating material is a high temperature liquid crystal polymer.

4. The catheter system of claim 1, wherein the first spline and the first ablation electrode are constructed from the same material.

5. The catheter system of claim 4, wherein the first spline and the first ablation electrode are constructed from a metal alloy of nickel and titanium.

6. The catheter system of claim 1, wherein the first spline and the second spline are configured to function as stimulation electrodes for evaluating success of renal denervation performed using the first ablation electrode and the second ablation electrode.

7. The catheter system of claim 6, wherein the first spline and the first ablation electrode are configured to operate as a bipolar pair of stimulation electrodes in one mode of operation, whereby the first ablation electrode is selectively operable as both an ablation electrode and a stimulation electrode.

8. The catheter system of claim 7, further comprising a third spline that includes a third ablation electrode and a fourth spline that includes a fourth ablation electrode.

9. The catheter system of claim 8, wherein the third spline and fourth spline are interconnected with an electrical wire to allow the third spline and the fourth spline to function as a stimulation electrode.

10. The catheter system of claim 1, wherein the electrode assembly further includes at least one thermocouple.

* * * * *